United States Patent
Stengel et al.

(10) Patent No.: US 11,771,124 B2
(45) Date of Patent: Oct. 3, 2023

(54) COMPOSITION COMPRISING MANNOSE OLIGOSACCHARIDE AND PROCESS FOR MAKING SAME AND USE THEREOF

(71) Applicant: CARGILL, INCORPORATED, Wayzata, MN (US)

(72) Inventors: Bruno Frédéric Stengel, Auderghem (BE); Christof Franz Küsters, Krefeld (DE)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 16/622,641

(22) PCT Filed: Jun. 14, 2018

(86) PCT No.: PCT/US2018/037484
§ 371 (c)(1),
(2) Date: Dec. 13, 2019

(87) PCT Pub. No.: WO2018/232078
PCT Pub. Date: Dec. 20, 2018

(65) Prior Publication Data
US 2020/0297019 A1  Sep. 24, 2020

(30) Foreign Application Priority Data
Jun. 14, 2017 (EP) .................... 17175981

(51) Int. Cl.
| | | |
|---|---|---|
| *A61K 31/702* | (2006.01) | |
| *A23L 33/125* | (2016.01) | |
| *A23K 20/163* | (2016.01) | |
| *A23K 50/30* | (2016.01) | |
| *A23K 50/60* | (2016.01) | |
| *A23K 50/75* | (2016.01) | |
| *A23L 33/00* | (2016.01) | |
| *A61K 8/60* | (2006.01) | |
| *A61Q 1/00* | (2006.01) | |
| *A61Q 11/00* | (2006.01) | |
| *A61Q 19/00* | (2006.01) | |

(52) U.S. Cl.
CPC .......... *A23L 33/125* (2016.08); *A23K 20/163* (2016.05); *A23K 50/30* (2016.05); *A23K 50/60* (2016.05); *A23K 50/75* (2016.05); *A23L 33/40* (2016.08); *A61K 8/60* (2013.01); *A61K 31/702* (2013.01); *A61Q 1/00* (2013.01); *A61Q 11/00* (2013.01); *A61Q 19/00* (2013.01); *A23V 2002/00* (2013.01); *A61K 2800/10* (2013.01)

(58) Field of Classification Search
CPC ..... A23L 33/125; A23L 33/40; A23K 20/163; A23K 50/30; A23K 50/60; A23K 50/75; A61K 31/702

USPC ........................................................ 514/53
See application file for complete search history.

(56) References Cited

U.S. PATENT DOCUMENTS

| | | |
|---|---|---|
| 6,559,302 B1 | 5/2003 | Shah et al. |
| 2013/0337109 A1 | 12/2013 | Hamaguchi |
| 2017/0173066 A1 | 6/2017 | Miller |

FOREIGN PATENT DOCUMENTS

| | | |
|---|---|---|
| EP | 2433970 A1 | 3/2012 |
| EP | 2662381 A1 | 11/2013 |
| JP | 6361003 A | 3/1988 |
| JP | 089989 A | 1/1996 |
| JP | 2003116536 A | 4/2003 |
| JP | 2003231694 A | 8/2003 |
| JP | 2004313074 A | 11/2004 |
| JP | 2009538872 A | 11/2009 |
| JP | 2012158526 A | 8/2012 |
| JP | 2013076044 A | 4/2013 |
| JP | 2014129334 A | 7/2014 |
| JP | 2017095377 A | 6/2017 |
| MX | 2016017105 A | 6/2018 |
| RU | 2358741 C2 | 6/2009 |
| WO | 20070138047 W | 12/2007 |
| WO | 2011091962 A1 | 8/2011 |
| WO | 2015160818 A1 | 10/2015 |
| WO | 2016122884 A1 | 8/2016 |
| WO | 2016122885 A1 | 8/2016 |
| WO | 2017112633 A1 | 6/2017 |

OTHER PUBLICATIONS

Huang et al. (Z. Naturforsch. 65 c, 387-390 (2010)).*
Sanz et al. (J. Agric. Food Chem. 2005, 53, 5192-5199).*
Brummer, Mieke, et al. The effect of yeast cell wall preparations on salmonella colonisation, gastrointestinal health and performance of broiler chickens. 2008. Tesis Doctoral. University of Pretoria.
Extraction and Deproteinization of Mannan Oligosaccharides, 2010, Z. Naturforsch, vol. 65c, p. 387-390.
K. Kummerer, Pharmaceuticals in the environment, Annual Review of Environment and Resources, 2010, V.35, p. 57-75, doi: 10.1146/annurev- environ-052809-161223 (see p. 60).
Ramirez-Hernandez, Alejandra; Rupnow, John; Hutkins, Robert W. Adherence reduction of Campylobacter lejuni and Campylobacter coli strains to HEp-2 cells by mannan oligosaccharides and a high-molecular-weight component of cranberry extract. Journal of food protection, vol. 78, No. 8, p. 1496-1505. 2015.

\* cited by examiner

*Primary Examiner* — Eric Olson (57) ABSTRACT

The present invention relates to a composition comprising mannose oligosaccharide and a process for making such. The present invention further relates to a composition comprising mannose oligosaccharide for use in the treatment of a human or animal.

17 Claims, 2 Drawing Sheets

FIG. 1

Recovery of mannose-oligosaccharides according to the present invention (Example 1) following *in vitro* treatment to simulate stomach acid conditions and to test its resistance to feed xylanases (Hostazym X microgranulate, Huvephama; Ronozyme WX, Novozymes)

FIG. 2

Heat map and cluster analysis showing differences on average abundance (n=16) of microbial population from broiler chicken ceca samples fed standard diet (NC) or diets supplemented with mannan-oligosaccharides originated from yeast (YMOS_1= BioMOS ®; YMOS_2= CELMANAX™) or according to the present invention Example 1 (SMOS)

COMPOSITION COMPRISING MANNOSE OLIGOSACCHARIDE AND PROCESS FOR MAKING SAME AND USE THEREOF

CROSS-REFERENCE TO RELATED APPLICATIONS

This application is a national phase application of International Application No. PCT/US2018/037484, filed Jun. 14, 2018, which claims the benefit of European Patent Application No. 17175981.4, filed Jun. 14, 2017, each of which is hereby incorporated by reference in its entirety.

FIELD OF THE INVENTION

The present invention relates to a composition comprising mannose oligosaccharide and a process for making such a composition. The present invention further relates to animal feed comprising the composition of the present invention. The present invention further relates to the composition according to the present invention for use in the treatment of human or animal, in particular for promoting growth and/or feed utilisation and/or reducing bacterial infections in human and animal.

BACKGROUND OF THE INVENTION

There is an existing demand for nutritional supplements for improving overall health, in particular gut health, in humans, farm animals, farmed fish and pets.

With world population increasing, the demand for animal proteins for human consumption is ever growing. The animal production industry is facing the challenge to breed more animals and this is done by increasing the animal population but also by increasing animal growth performance and improving animal health in general. Animal health and animal growth performance are key factors for successful animal farming. In particular, gastrointestinal health and gastrointestinal integrity are essential factors when it comes to animal growth performance, and feed additives are used to achieve this. Another main issue is bacterial contamination, particularly true in poultry and pigs. A widely used method in animal farming to counter bacterial contamination is for example the use of substances which, instead of killing bacteria (such as antibiotics do), rather reduce the undesirable bacterial population in the animal by a binding mechanism preventing harmful bacteria from attaching to the surface of the intestinal tract.

Also, bacterial contamination in food represents an important food safety issue and must be managed and reduced. In particular contamination with *Salmonella* and *E. coli* are important issues in the food supply chain.

Mannose oligosaccharide compositions are known to improve overall health, in particular gut health. Existing mannose oligosaccharide (or manno-oligosaccharide, or MOS) compositions currently on the market are all extracts, such as yeast extracts, mostly yeast cell wall extracts, green coffee beans extracts, konjac extracts and so on. They all present the disadvantage of not being highly pure compositions and not having consistent compositions, particularly true for yeast cell wall extracts, and consequently their action in animal is not very predictable and their effects are very much fluctuating. Also, most of them are not soluble in water. As a consequence, their application in liquid feed and drinking water is not practical and thus limited. Further, the production process of such mannose oligosaccharide compositions has a non-negligible environmental impact, due to the generation of many waste streams.

WO2015160818 A1 relates to the production of enriched yeast cell wall compositions, comprising soluble yeast cell wall MOS.

There is thus clearly still a need to provide more efficient feed additives. Also there is a need to provide feed additives that are produced in a more environmental friendly way. The present invention addresses those needs.

SUMMARY OF THE INVENTION

In a first aspect, the present invention relates to a composition comprising mannose oligosaccharide ("mannose oligosaccharide composition of the present invention"), characterized in that said composition is soluble in water.

In a further aspect, the present invention relates to a food, animal feed, fish feed or pet food product comprising the mannose oligosaccharide composition of the present invention and further food, animal feed or pet food ingredients.

In a further aspect, the present invention relates to a personal care or pharmaceutical composition comprising the mannose oligosaccharide composition of the present invention and further personal care or pharmaceutical ingredients.

In a further aspect, the present invention relates to a cosmetic, personal care or pharmaceutical product comprising the mannose oligosaccharide composition of the present invention.

In a further aspect, the present invention relates to a process for making a composition comprising mannose oligosaccharide characterized in that it comprises the steps of
  a) Polycondensing mannose by passing the mannose through a microreactor at a temperature of from 180° C. to 240° C., preferably from 195° C. to 240° C. in the presence of an acidifying catalyst to produce a manno-oligosaccharide containing composition,
  b) Optionally neutralising and/or decolorizing the manno-oligosaccharide composition,
  c) Optionally refining the manno-oligosaccharide composition,
  d) Collecting the manno-oligosaccharide composition.

In a further aspect, the present invention relates to the use of the mannose oligosaccharide composition of the present invention for treating a human or an animal or the mannose oligosaccharide composition for use in treating a human or an animal.

BRIEF DESCRIPTION OF THE FIGURES

The drawings illustrate generally by way of example but not by way of limitation various examples of the present invention.

DETAILED DESCRIPTION

The use of "a" or "an" to describe the various elements or components herein is merely for convenience and to give a general sense of the invention. This description should be read to include one or at least one, and the singular also includes the plural unless it is obvious that it is meant otherwise.

In the present description, the terms mannose oligosaccharide, manno-oligosaccharide and MOS are used interchangeably to describe the same. Mannose oligosaccharide is defined as an oligosaccharide of mannose having a DP of 3 or more. DP refers to the degree of polymerisation, i.e. the number of monomers present in the oligosaccharide. In mannose oligosaccharide, the monomer is mannose. The mannose oligosaccharide composition of the present invention comprises mannose oligosaccharides having a DP of 3 or more and is characterized in that it is a source of mannose disaccharide, further it may comprise mannose monosaccharide. HPLC analysis (ISO 10504:1998-10) may be done to determine the amount and type of the various saccharide present in the mannose oligosaccharide composition, such as DP1, DP2, DP3 and higher.

The invention is defined in the appended claims. At least one aspect of the invention is based on the finding that the composition comprising mannose oligosaccharide according to the present invention ("composition of the present invention" or "mannose oligosaccharide composition of the present invention") has improved effects in a human and in an animal, compared to existing MOS compositions. The improved effects of the MOS composition of the present invention are, amongst others, an improved effect on physical performance in human, an improved effect on growth performance in animal and further an improved effect on digestive health, bacterial/pathogen load control, in particular bacterial binding; an improved impact on the immune system, an improved prebiotic effect, an improved antimicrobial effect, an improved anti-bacterial effect, than currently known MOS compositions.

The current invention relates to a composition comprising mannose oligosaccharide characterized in that the composition is soluble in water. The composition of the present invention has a solubility of 20% or more, more preferably of 30% or more, even more preferably of 40% or more, yet even more preferably of 50% or more, yet even more preferably of 60% or more. The solubility of the composition of the present invention may thus range from 20 to 90%, more preferably from 30 to 85%, yet even more preferably from 40 to 80%, yet even more preferably from 50 to 75%, most preferably from 60 to 75%. Solubility may be measured according to test A as described hereafter.

Test A

A 10 wt % aqueous solution of the composition to be measured is provided, heated up to 40° C. and kept at 40° C. for 1 hour.

The composition is then filtered over a 0.45 µm pore size filter to remove any undissolved material and the filtrate is recovered.

The filtrate is then submitted to HPLC analysis (ISO 10504: 1198-10) and the results are recorded Solubility is expressed in % and corresponds to the total saccharide content in the filtrate compared to the dry matter of the initial 10 wt % aqueous solution.

The MOS composition according to the present invention can be readily dissolved in water. It forms a clear solution in water.

Preferably, the MOS composition of the present invention is further characterized in that it comprises less than 0.1 wt % db, preferably less than 0.01 wt % db, more preferably less than 0.001 wt % db of beta-glucan most preferably the MOS composition of the present invention does not comprise beta-glucan. Mannose oligosaccharide of the prior art contain high amounts of beta-glucan, typically in a ratio mannose-oligosaccharide:beta-glucan of 1:1. These compositions are believed to have an effect on the immune system due to the high content of beta-glucan. It has surprisingly been found that the compositions of the present invention have an effect on the immune system, which may be similar to the effect obtained with prior art composition, even though the compositions of the present invention contain very low amounts to no beta-glucan as described above.

Further, the MOS composition is characterized in that it is not derived from yeast or vegetable fibers, such as from konjac or from coffee beans.

Preferably, the MOS composition of the present invention is further characterized in that the mannose oligosaccharide content is from 30 weight % (wt %) or higher, preferably from 40 wt % or higher, more preferably from 50 wt % or higher, even more preferably 60 wt % or higher, yet even more preferably from 65 wt % or higher, yet even more preferably of 70 wt % or higher, yet even more preferably of 80 wt % or higher, on dry basis of the composition (db).

The MOS composition of the present invention is preferably a source of mannose disaccharide (DP2). Thus preferably the MOS composition of the present invention has a content of DP2, of from 10 to 35 wt % db, preferably of from 15 to 30 wt % db, preferably of from 20 to 25 wt % db. The content of DP2 may be about 30 wt % db. The content of DP2 may be about 3 1wt % db. The content of DP2 may be about 32 wt % db. The content of DP2 may be about 33 wt % db. The content of DP2 may be about 34 wt % db. The content of DP2 may be about 35 wt % db.

Further, the MOS composition may contain fructose, in an amount of up to 10 wt % db, such as from 0.5 to 10 wt % db, preferably up to 5 wt % db, more preferably up to 3 wt % db, more preferably up to 1 wt % db.

Further, the MOS composition may contain mannose in an amount of from 5 to 50 wt % db, preferably from 5 to 25 wt % db.

Further, the MOS composition may contain glucose, in an amount of from 1 to 15 wt % db, preferably 5 to 10 wt % db.

The dry substance of the MOS composition can be adapted to the need of its application. The dry substance may be at least 70 wt %, preferably at least 75 wt %, more preferably at least 80 wt %, even more preferably at least 90 wt %, yet even more preferably at least 95 wt %, such as for example from 95 to 99 wt %. The MOS composition can be stored either in powder form or in liquid form depending on the intended use. In powder form, the MOS composition of the present invention is a stable, yellowish to white, free flowing powder.

Further, the MOS composition may be characterised in that the mannose oligosaccharide comprises predominantly alpha- & beta-1,6 and alpha-1,3 type linkages. Preferably at least 50%, more preferably at least 75%, even more preferably at least 80% of the linkages are alpha- & beta-1,6 and alpha-1,3 type linkages. Methods for measuring the various types of linkages which may be present in saccharides are well known in the art, such as High Performance Anion Exchange with Pulsed Amperometric Detection Detection (HPAE-PAD).

It has been found that the MOS composition according to the present invention has an improved effect on the growth performance of animals when the animals are fed with said composition. The growth performance of animals is understood to be the weight gain and feed intake of the animal. In particular, MOS compositions of the present invention characterized in that DP2 is higher than 25 wt % db, for examples from 25 to 30 wt % db have a further improved effect on the growth performance of animals. More in particular, MOS compositions of the present invention further characterized in that DP3+ content is of 40 wt % db or lower, for example from 35 to 40 wt % db have a further improved effect on the growth performance of animals.

Further it has been found that MOS composition according to the present invention is able to modulate the immune system, i.e. able to modulate the response of immune cells or macrophages. Therefore the present invention further relates to a MOS composition according to the present invention for use in modulating the response of immune cells or macrophages. The present invention further relates to the use of a MOS composition according to the present invention to modulate the response of immune cells or macrophages.

Further, it has been found that the MOS composition according to the present invention increase proliferation of epithelial cells. The MOS composition is useful to repair lesions in animal mucosa, such as the intestinal mucosa by stimulating the proliferation of enterocytes. Therefore the present invention further relates to a MOS composition according to the present invention for use in increasing proliferation of epithelial cells. The present invention further relates to the use of a MOS composition according to the present invention to increase the proliferation of epithelial cells.

Further it has been found that the MOS composition according to the present invention is useful to reduce pathogen load, in particular bacterial or microbial load, and/or infections in or on humans or animals. Therefore the present invention further relates to a MOS composition according to the present invention for use in reducing pathogen load, in particular bacterial or microbial load, and/or infections in or on humans or animals, in particular in the gastro intestinal tract of animals or humans. The present invention further relates to the use of a MOS composition according to the present invention to reduce pathogen load, in particular bacterial or microbial load, and/or infections in or on humans or animals.

The invention further relates to a MOS composition according to the present invention for use in antimicrobial treatments in or on humans or animals. The invention also relates to the use of the MOS composition according to the present invention in antimicrobial treatments, therapeutic or non-therapeutic, in or on humans or animals. Such treatments may be for example in the form of a cosmetic product or a personal care product, such as a skin care product, or a pharmaceutical product.

In particular, a MOS composition characterized in that DP2 is from 15 to 25 wt % db, such as about 22 wt % db, and DP3+ is from 45 to 60 wt % db, such as about 50 wt % db, and also in particular a MOS composition characterized in that DP2 content is from 10 to 20 wt % db and DP3+ content is from 55 to 75 wt % db, such as higher than 60 wt % db, such as from 60 to 70 wt % db, preferably from 65 to 70 wt % db, are useful to reduce *E. coli* infections and/or *Salmonella* infections in animal.

The present invention further relates to the use of the MOS composition as described herein for treating human or animal. The present invention further relates to the MOS composition as described herein for use in treating human or animal. The MOS composition as described herein may thus also be used in/as a medicament for treating human or animal.

The present invention further relates to the use of MOS composition as described herein for improving the growth performance of animals, including the non-therapeutic use thereof for improving the growth performance of animals. The MOS composition as described herein may also be used in/as a medicament for improving the growth performance of animals. The MOS composition may be used as a feed additive.

The present invention further relates to the use of MOS composition of the present invention to reduce microbial or bacterial contamination or to reduce infections in or on humans and animals, preferably for reducing contamination with *Salmonella* and/or *E. coli*. Therefore, the invention also covers the MOS composition as described herein for use in reducing microbial or bacterial contamination or for use in reducing infections in or on humans or animals, preferably for use in reducing contamination with *Salmonella* and/or *E. coli*. Particularly, MOS composition with about 22% DP2 and 50% DP3+ (±1%) are useful; and also MOS composition with DP3+ higher than 60% are useful.

The present invention further relates to the MOS composition as described herein for improving weight gain and/or improving feed intake and/or improving body weight and/or improving stool quality in humans or animals. This includes both the therapeutic and non-therapeutic use thereof in improving weight gain and/or improving feed intake and/or improving body weight and/or improving stool quality in humans or animals.

The present invention further relates to the MOS composition as described herein for reducing or preventing bacterial attachment to the intestinal mucosa. This includes the MOS composition as described herein for use in reducing or preventing bacterial attachment to the intestinal mucosa.

Preferably the animal is poultry (such as chicken, turkey, and quail), pig, ruminants, horses, aquatic animals (such as fish, e.g. salmon or trout, and shrimps), or pets. More preferably the animal is poultry or pig. It has been shown in in vivo trials, as exemplified in the example section below, that the intake of MOS composition according to the present invention is beneficial to the gastrointestinal health of the animals and increases the growth performance of the animals.

The present invention further relates to a food, animal feed, or pet food product comprising the MOS composition of the present invention and further food, animal feed or pet food ingredients.

An advantage of using the MOS composition of the present invention is that it can readily be dissolved, it can be better handled and/or dosed and is thus very suitable for use in many applications using at least one liquid ingredient, such as for example liquid food, such as beverages; or in liquid feed such as drinking water for animals. Also in dry mixes, the MOS composition can be easily incorporated.

The food product can be a bakery product such as biscuits, cookies, cereal bars, breakfast cereals, crackers, cakes, breads, muffins, pastries, fried baked goods and the like.

The food product can be a convenience product such as sauces, puddings, soups.

The food product can be a confectionery product, such as chocolate, chocolate like products, soft candies, hard candies, hard boiled candies, pressed candies, gums, chewing gums, jellies, marshmallows, lozenges, tablets, caramel, nougats, pralines, toffees, fudge, fondant, marzipan and the like.

The food product can be a beverage. Beverage includes any syrup or any alcoholic and non-alcoholic, carbonated and non-carbonated or drinkable solution including waters, beers, lemonades, cordials, iced tea, fruit juices, vegetable based beverages such as cereal based beverages, almond based beverages or other nut based beverages, soy based beverages, rice based beverages, and the like. It also encompasses beverage concentrates and drink powders. Beverage concentrate refers to a concentrate that is either in liquid form or in essentially dry mixture form. The beverage concentrate is usually formulated to provide a drinkable beverage composition or a final beverage when constituted or diluted with water, either carbonated or non-carbonated. Drink powders are suitable for constituting a final beverage with water, carbonated or non-carbonated, or milk.

The food product can be dairy product such as milk, whey, yogurt and drinks based on them; dairy cocoa based drinks, fermented desserts (such as fresh cheese preparations, drinkable products), ice cream, milk shakes, frozen yoghurt, neutral dairy desserts (such as puddings, flans, créme desserts, whipped desserts) and flavoured yoghurt preparations (e.g. fruit yoghurt without fruit), frozen dairy desserts and the like.

The food product can also be baby food, infant food and food supplements.

The food product can also be food specifically designed for the needs of elderly.

The animal feed product may be a feed product designed for feeding pig, preferably piglet, or chicken, such as a feed for broilers or a feed for layers, or fish feed, such as salmon or trout. The animal feed may also be horse feed. Said pig feed, chicken feed, fish feed or horse feed comprise next to the MOS composition of the present invention, feed ingredients typically or specifically used for such animal feed. The person skilled in the art of preparing animal feed is aware of typical and specific compositions of animal feed. The MOS composition is also very suitable to be used as feed supplement. As it is soluble, it can easily be added to the drinking water for example. Further feed ingredients of the feed product may be other carbohydrates and fibres such as glucans, arabinoxylan oligosaccharides, proteins, fats, vitamins, minerals and the like. Depending on the animal species, the composition of the feed will vary; the skilled person understands how to formulate suitable feed compositions.

Preferably, the MOS composition is present in the food, animal feed or pet food product in such an amount as to provide from 0.01 to 20 g, preferably from 0.01 to 10 g of the MOS composition per kg of body weight of the human, animal or pet per day, in one or more servings. Preferably, in particular for animal or pet, the MOS composition is present in the animal feed or pet food product in such an amount as to provide from 0.01 to 0.02 g of the MOS composition per kg of body weight of the animal or pet per day, in one or more servings. In particular, the food, animal feed or pet food may comprise from 0.02 to 0.6 wt % of the present MOS composition, based on the weight of the food, animal feed or pet food product.

In one aspect, the food, animal feed or pet food, preferably pig feed comprises from 0.1 to 0.5 wt %, preferably from 0.1 to 0.4 wt %, even more preferably from 0.1 to 0.3 wt %, yet even more preferably from 0.1 to 0.2 wt % of the MOS composition of the present invention, based on the weight of the food, animal feed or pet food product.

In another aspect, the food, animal feed or pet food, preferably poultry feed comprises from 0.01 to 0.05 wt %, preferably from 0.01 to 0.04 wt %, even more preferably from 0.01 to 0.03 wt %, yet even more preferably from 0.01 to 0.02 wt % of the MOS composition of the present invention, based on the weight of the food, animal feed or pet food product.

Further, the present invention relates to a cosmetic product comprising the MOS composition of the present invention and further cosmetic product ingredients, particularly in products having antimicrobial properties. Cosmetic products can be make-up creams, make-up lotions, lipsticks and the like. Preferably the cosmetic product may comprise from 0.01 to 30 wt %, preferably from 0.01 to 20 wt %, more preferably from 1 to 15 wt %, even more preferably from 5 to 10 wt % of the present MOS composition, based on the weight of the cosmetic product. The present invention also relates to the use of the MOS composition in cosmetic products. In particular, the present invention also relates to the use of the MOS composition in cosmetic products having anti-microbial properties.

The present invention also relates to a personal care product comprising the MOS composition of the present invention and further personal care product ingredients, particularly in products having antimicrobial properties. Personal care products may be body lotions, oral care products (mouth washes, toothpastes and the like), hair care products, hygiene products, such as hand gel, wet hand towels or wipes (baby wipes, intimate wipes, cleansing make-up removal wipes) and the like. Also included under personal care products are skin care products, such as cleansing lotions and solutions, face and hand creams, body lotions, moisturisers, acne-treatment products, deodorants and the like. Preferably, the personal care product may comprise from 0.01 to 30 wt %, preferably from 0.01 to 20 wt %, more preferably from 1 to 15 wt %, even more preferably from 5 to 10 wt % of the present MOS composition based on the weight of the personal care product. The present invention also relates to the use of the MOS composition according to the present invention in personal care products. In particular, the MOS composition according to the present invention is useful for personal care products having anti-microbial properties.

The present invention also relates to a pharmaceutical product comprising the MOS composition of the present invention and further pharmaceutical ingredients. Personal care product may be hand creams. Pharmaceutical products include disinfectants, antiseptic balm and the like.

Preferably the pharmaceutical product may comprise from 0.01 to 20 wt % of the present MOS composition based on the weight of the pharmaceutical product.

The invention further relates to a process for making a manno-oligosaccharide composition, said process comprises the steps of:
a) Polycondensing mannose by passing the mannose through a microreactor at a temperature of from 180° C. to 240° C., preferably 195° C. to 240° C., in the presence of an acidifying catalyst to produce manno-oligosaccharide containing composition,
b) Optionally neutralising and/or decolorizing the manno-oligosaccharide composition,
c) Optionally refining the manno-oligosaccharide composition,
d) Collecting the manno-oligosaccharide composition.

The mannose may be a mannose containing composition, isolated mannose, a mannose solution or a mixture of these. Preferably the mannose is an aqueous mannose solution. The concentration of the mannose in the aqueous mannose solution is not important, however, it is advantageous to have the aqueous mannose solution as concentrated as possible consistent with viscosity requirements. Therefore, it is advantageous that the aqueous mannose solution comprises from 10 to 90 wt % dry substance, preferably from 15 to 80 wt % dry substance, more preferably from 40 to 70 wt % dry substance, even more preferably from 50 to 60 wt % dry substance. Most preferably the aqueous mannose solution comprises from 75 to 90 wt % dry substance.

The amount of acidifying catalyst used is preferably in a weight ratio to mannose of mannose:acidifying catalyst 100:0.005 to 100:20, more preferably from 100:0.5 to 100:10, even more preferably from 100:1 to 100:5.

Preferably the acidifying catalyst is citric acid, sulphuric acid and/or phosphoric acid.

Preferably, the acidifying catalyst is mixed with the mannose before it is passed through the microreactor.

Preferably the temperature of step a) is from 180° C. to 230° C., more preferably 195° C. to 230° C., more preferably 195° C. to 220° C., even more preferably from 195° C. to 210° C., and yet even more preferably from 195° C. to 200° C.

The residence time of the mannose containing composition in the microreactor during step a) is preferably from 5 to 20 seconds, more preferably from 10 to 15 seconds.

Preferably, before step a), the mannose is passed through a first microreactor in the presence of the acidifying catalyst at a lower temperature than the temperature of step a) described above. Said lower temperature is preferably from 100° C. to 180° C., more preferably from 120° C. to 175° C., even more preferably from 140° C. to 170° C., even more preferably from 150° C. to 165° C. Some polycondensation may already take place during this step. Preferably the residence time of the mannose containing composition in the first microreactor is quite short, such as 5 seconds or lower, preferably 4 seconds or lower, more preferably 3 seconds or lower, even more preferably 2 seconds or lower, such as from 0.5 to 2 seconds or from 0.5 to 1 second.

The first microreactor and the microreactor of step a) can have the same configuration, they may be similar, and they may even be the same microreactor, when the process is performed batch wise for example. The process of the present invention can run in batch, semi-continuous, pulse or continuous manner, preferably it is run in a continuous manner.

Thus preferably, the present invention relates to a process comprising
  a0) Passing mannose through a microreactor at a temperature of from 100° C. to 180° C. in the presence of an acidifying catalyst to obtain a heated mannose,
  a) Polycondensing the heated mannose through a microreactor at a temperature of from 180° C. to 240° C., preferably 195° C. to 240° C. in the presence of the acidifying catalyst,
  b) Optionally neutralising and/or decolorizing the manno-oligosaccharide composition,
  c) Optionally refining the manno-oligosaccharide composition,
  d) Collecting the manno-oligosaccharide composition,
Wherein the acidifying catalyst is preferably citric acid, sulphuric acid and/or phosphoric acid.

If needed before collecting the manno-oligosaccharide composition or after step c) and/or d), a cooling step may be done to reduce the temperature of the manno-oligosaccharide composition.

Preferably the manno-oligosaccharide composition is neutralised. Neutralising the manno-oligosaccharide composition may be done until the composition reaches a pH of from 4 to 7. This is advantageous for an increased stability of the product, e.g. less hydrolysis over time and thus less to no change in composition of the product. Also an advantage is that the product is then suitable for use with other ingredients that are sensitive to acids or acidic conditions. Neutralisation may be done with any suitable base. Preferably, in particular when the manno-oligosaccharide composition is to be used in food and maybe also in feed and pet food, the base is caustic and/or potassium hydroxide.

It should be noted that it is possible to either neutralise the manno-oligosaccharide composition or to decolorize the manno-oligosaccharide composition or to do both.

Preferably the manno-oligosaccharide composition is refined. Refining the produced manno-oligosaccharide composition may be done by passing it over series of anionic and cationic resins, and/or a polisher such as active carbon and/or by chromatography. In particular refining may be done to remove part or all mannose from the composition. This is particularly advantageous when the manno-oligosaccharide composition is to be used in food applications.

The present invention further relates to a MOS composition obtainable by the process of the present invention. Indeed such MOS composition has, amongst others, the improved effects as discussed herein.

The present invention will be illustrated by the following non-limiting examples.

EXAMPLE

Example 1: Production of MOS Composition

A mannose solution (C*TruSweet 016Ko from Cargill) containing 90 wt %+/−2% of mannose on a dry basis is blended with solid citric acid at a weight ratio of 100:3 on a dry basis. The resulting solution is evaporated via a thin-film evaporator up to a dry substance of 85%+/−1%. The solution is then heated to 165° C. by pumping it through a micro heat exchanger (Kreuzxtrom-reaktormodul 1694-X-19.0, KIT, IMVT) at a constant flow rate of 15 kg/hr with an overall residence time shorter than 2 seconds. The material is then pumped through a second micro heat exchanger (Kreuzxtrom-reaktormodul 2155-A-4.0, KIT, IWVT) for a period of 11 seconds at a temperature of 195° C., where the main polycondensation reaction takes place.

The resulting polycondensation product (mannose oligosaccharide composition) is diluted with lye water to obtain a solution with 50 wt % solid content and a pH of 5+/−0.2. The solution is then cooled down to 50° C. The HPLC analysis (ISO 10504:1998-10) shows a manno-oligosaccharide, i.e. DP3+, content of 40 wt %.

Example 2: Production of MOS Composition

A mannose solution (C*TruSweet 016Ko from Cargill) containing 90 wt %+/−2% of mannose on a dry basis is blended with solid citric acid at a weight ratio of 100:3 on a dry basis. The resulting solution is evaporated via a thin-film evaporator up to a dry substance of 85%+/−1%. The solution is then heated to 170° C. by pumping it through a micro heat exchanger (Kreuzxtrom-reaktormodul 1694-X-19.0, KIT, IMVT) at a constant flow rate of 15 kg/hr with an overall residence time shorter than 2 seconds. The material is then pumped through a second micro heat exchanger (Kreuzxtrom-reaktormodul 2155-A-4.0, KIT, IWVT) for a period of 11 seconds at a temperature of 200° C., where the main polycondensation reaction takes place.

The resulting polycondensation product (mannose oligosaccharide composition) is diluted with lye water to obtain a solution with 50 wt % solid content and a pH of 5+/−0.2. The solution is then cooled down to 50° C. The HPLC analysis (ISO 10504:1998-10) shows a manno-oligosaccharide, i.e. DP3+, content of 50 wt %.

Example 3: Comparative Example

MOS according to the present invention (composition A and composition B, respectively made according to example 1 and 2) is compared to MOS compositions available on the market (samples C to I) which are derived from yeast.

Solubility is determined according to test A as described above.

Results show that all commercial yeast-derived samples have a solubility lower than 4 wt %, which is well below the solubility of the product of this invention.

TABLE 1

Sugar profile of mannan-oligosaccharides (MOS) samples determined by HPLC and solubility.

| Product | Dextrose (% db) | Galactose (% db) | DP2 + of mannose | Solubility (%) |
|---|---|---|---|---|
| Composition A | 2.6 | — | 65.6 | 68.2 |
| Composition B | 3.4 | — | 73.8 | 77.2 |
| Nutri-MOS (C) | <0.1 | 0.2 | <0.1 | 0.4 |
| Pareti (D) | — | — | — | 0 |
| ECHOMOS (E) | — | 0.1 | — | 0.1 |
| ASCO-MOS (F) | 0.1 | — | — | 0.1 |

Stability to Acid and Feed Enzymes

Figure 1:
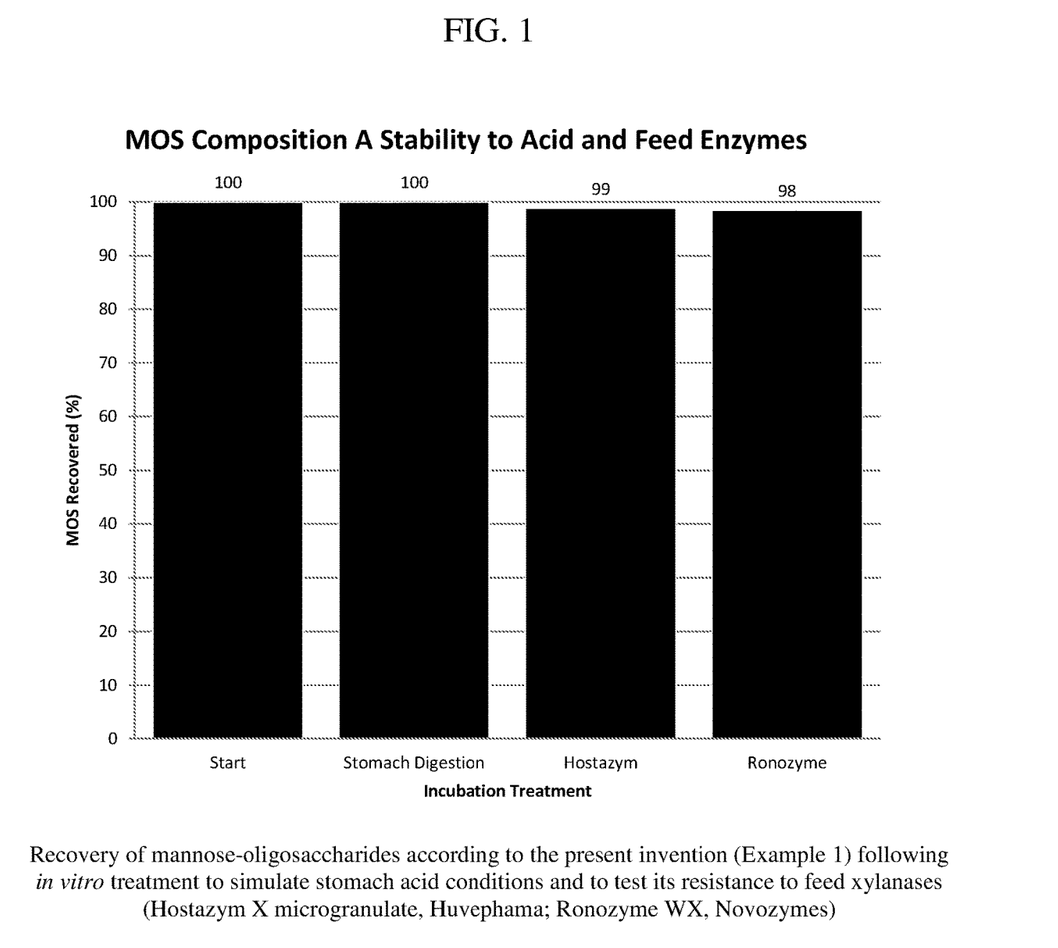
FIG. 1 shows MOS composition A stability to acid and feed enzymes as outlined in Example 3.

A sample of a commercially available MOS extracted from yeast (BioMOS®) and a sample of MOS composition according to the present invention made according to example 1 are incubated for 2 hours at 41° C. (chicken physiological internal temperature) under condition to stimulate stomach acids (pH 2 for first 30 min, then pH 7) or at neutral pH 7 with and without two xylanazes commercially used in feed. The dose of enzyme in buffer was adjusted based on supplier recommendation for feed and previously proven to work in xylan samples in vitro under the same conditions. Results in FIG. 1 demonstrate that feed enzymes do not degrade MOS composition according to the present invention independent of stomach acid conditions. Results for BioMOS® could not be obtained since it remains insoluble and therefore could not be analysed by HPLC.

Example 4: In Vitro and Ex-Vivo Trials

The effect of mannan-oligosaccharides (MOS) according to the present invention was compared to that of commercially available yeast-derived MOS in vitro.

Minimal Inhibition Concentration (MIC)

In the first assay, the effect of different concentrations of MOS on the growth of pathogenic bacteria, *E. coli* and *Salmonella*, was accessed to determine the minimal inhibition concentration (MIC) of each material. The materials were added at different dilutions into wells on a 96 well plate that was spiked with 10×CFUs of the respected pathogenic bacteria (*E. coli* or *Salmonella*). The plate was incubated for 48 hours and the colony forming units (CFU) were determined by plate counting for each well and calculated as % of pure media. Results of MIC assays are reported in Tables 2 and 3.

TABLE 2

Minimal Inhibition Concentration (MIC) for *E. coli* and *Salmonella* determined in vitro for different MOS compositions.

| Concentration % | Comp A | | Comp B | | Concentration % | Celmanax | | Safmannan | |
|---|---|---|---|---|---|---|---|---|---|
| | Mean | SEM | Mean | SEM | | Mean | SEM | Mean | SEM |
| *E. coli* | | | | | | | | | |
| 10 | 56 | 11 | 66 | 15 | 5 | 11 | 1 | 228 | 8 |
| 1 | 85 | 11 | 86 | 8 | 0.5 | 172 | 14 | 164 | 8 |
| 0.1 | 82 | 4 | 84 | 2 | 0.05 | 105 | 1 | 113 | 5 |
| 0.01 | 95 | 3 | 95 | 1 | 0.005 | 92 | 1 | 90 | 3 |
| *Salmonella* | | | | | | | | | |
| 10 | 45 | 6 | 57 | 6 | 5 | 21 | 7 | 180 | 3 |
| 1 | 90 | 5 | 97 | 2 | 0.5 | 136 | 2 | 137 | 1 |
| 0.1 | 95 | 1 | 98 | 1 | 0.05 | 109 | 1 | 114 | 1 |
| 0.01 | 101 | 3 | 101 | 3 | 0.005 | 99 | 2 | 98 | 2 |

Comp A: MOS composition according to example 1
Comp B: MOS composition according to example 2
CELMANAX ™ and SafMannan ®: commercially available yeast derived MOS TABLE 1-continued Sugar profile of mannan-oligosaccharides (MOS) samples determined by HPLC and solubility.

| Product | Dextrose (% db) | Galactose (% db) | DP2 + of mannose | Solubility (%) |
|---|---|---|---|---|
| Actigen (G) | 0.1 | — | — | 0.1 |
| Bio-MOS ® (H) | — | — | — | 0 |
| Zorien (I) | 0.2 | — | — | 0.2 |

TABLE 3

Minimal Inhibition Concentration (MIC) for *E. coli* and *Salmonella* determined in vitro for two batches of the two compositions of MOS according to the present invention.

| Concentration (%) | Comp A-Batch 1 | Comp A-Batch 2 | Comp B-Batch 1 | Comp B-Batch 2 | Postive Control |
|---|---|---|---|---|---|
| *E.Coli* | | | | | |
| 10 | 0.65 | 0.64 | 0.70 | 0.63 | 0.62 |
| 5 | 0.64 | 0.62 | 0.69 | 0.62 | |
| 2.5 | 0.63 | 0.68 | 0.73 | 0.66 | |
| 1.25 | 0.73 | 0.67 | 0.85 | 0.80 | |
| 0.625 | 0.89 | 0.88 | 0.76 | 0.85 | |
| 0.3125 | 0.80 | 0.81 | 0.74 | 0.75 | |
| 0.15625 | 0.76 | 0.73 | 0.66 | 0.70 | |
| 0.078125 | 0.76 | 0.73 | 0.70 | 0.70 | |
| *Salmonella* | | | | | |
| 10 | 0.45 | 0.44 | 0.52 | 0.43 | 0.79 |
| 5 | 0.56 | 0.61 | 0.64 | 0.60 | |
| 2.5 | 0.60 | 0.63 | 0.62 | 0.61 | |
| 1.25 | 0.58 | 0.61 | 0.69 | 0.61 | |
| 0.625 | 0.77 | 0.62 | 0.75 | 0.75 | |
| 0.3125 | 0.77 | 0.77 | 0.76 | 0.75 | |

TABLE 3-continued

Minimal Inhibition Concentration (MIC) for *E. coli*
and *Salmonella* determined in vitro for two batches of the
two compositions of MOS according to the present invention.

| Concentration (%) | Comp A-Batch 1 | Comp A-Batch 2 | Comp B-Batch 1 | Comp B-Batch 2 | Postive Control |
|---|---|---|---|---|---|
| 0.15625 | 0.77 | 0.77 | 0.76 | 0.76 | |
| 0.078125 | 0.80 | 0.77 | 0.76 | 0.77 | |

Comp A: MOS composition according to example 1, two batches were produced, batch 1 and 2
Comp B: MOS composition according to example 2, two batches were produced, batch 1 and 2

These results show that MIC of the MOS compositions A and B start to inhibit bacteria growth by 20% when added at concentrations higher than 1% in solution. Bacteria inhibitory effects above 50% were achieved only at concentrations higher than 10% (Tables 2 and 3). Based on these findings we can conclude that the MOS compositions of the present invention have limited capacity to kill *E. coli* and *Salmonella* directly so they are not bactericidal. The yeast-derived MOS samples, CELMANAX™ and SafMannan® did not show equivalent inhibition capacity compared to MOS according to the present invention. They showed inhibition only when reaching 10% concentration but in contrast to the MOS compositions of this invention they had no effect or a growth stimulatory effect on *E. coli* and *Salmonella* at lower concentrations (Table 2).

Inhibition of Biofilm Formation

The effect of MOS compositions according to the present invention and that of some commercially available yeast derived MOS on bacteria biofilm formation on abiotic surface is tested in vitro. The compounds are added at different dilutions (10%, 1%, 0.1% and 0.01%) into wells on a 96 well plate that was spiked with 10×CFUs of the respected pathogenic bacteria (*E. coli* or *Salmonella*). The plate is incubated for 48 hours at 37° C. The liquid on each well is removed and the well is washed with PBS buffer before the biofilm cells attached to the plastic surface are stained with crystal violet and eluded using ethanol. The colour intensity of the dye is measured on a spectrophotometer at 490 wave length as absorbance (OD). The values are calculated as % of blank control (buffer solution, enriched media and inoculated bacteria). The results of these measurements can be seen in Table 4.

The results show that the MOS compositions of the present invention can inhibit biofilm formation on a dose-dependent manner starting with more than 40% inhibition with concentration as low as 0.01% and achieving 79% inhibition for *E. coli* and 92% inhibition for *Salmonella* at 10% concentration in solution. Yeast-derived MOS only showed inhibitory effects of about 70% at 10% concentration and, in the case of *salmonella*, they showed even high stimulus of biofilm formation at lower concentrations (Table 4).

Inhibition of Pathogens Adhesion to Intestinal Surface Ex-Vivo

Two different assays were used to evaluate the interference of MOS compositions according to the present invention and commercially available yeast-derived MOS (CELMANAX™ and SafMannan®) on the capacity of *E. coli* and *Salmonella* to adhere to the surface of live enterocyte cells. The assay used ceca tissue collected from actual birds and mounted in Ussing chambers. The luminal side of the epithelium was incubated with a Ringer's based buffer solution at 37° C. containing *E. coli* or *Salmonella* and a certain concentration of the test product. After 90 minutes incubation time, the surface is washed, homogenized and plated to enumerate pathogenic bacteria attached to the tissue. The results of these assays are presented in Tables 5 to 8.

TABLE 5

Effect of different MOS sources on relative adhesion of *Salmonella* to chicken ceca tissue ex-vivo

| MOS | Adhesion | Reduction (%) |
|---|---|---|
| No Treatment | 1.00 | 0 |
| BioMOS | 0.40 | −60 |
| Celmanax | 0.69 | −31 |
| Safmannan | 0.73 | −27 |
| Composition A | 0.53 | −47 |
| Composition B | 0.62 | −38 |

Composition A: MOS composition according to example 1
Composition B: MOS composition according to example 2
CELMANAX ™ and SafMannan ®: commercially available yeast derived MOS

TABLE 4

Dose effect of MOS compositions on relative percent inhibition
(compared to control) of biofilm formation on abiotic surfaces in vitro

| Concentration | Comp A | | Comp B | | Concentration | Celmanax | | Safmannan | |
|---|---|---|---|---|---|---|---|---|---|
| % | Mean | SEM | Mean | SEM | % | Mean | SEM | Mean | SEM |
| *E. coli* | | | | | | | | | |
| 10 | 21 | 1 | 22 | 2 | 5 | 35 | 2 | 593 | 111 |
| 1 | 30 | 3 | 30 | 2 | 0.5 | 733 | 56 | 543 | 70 |
| 0.1 | 50 | 6 | 53 | 4 | 0.05 | 120 | 13 | 121 | 12 |
| 0.01 | 58 | 2 | 52 | 2 | 0.005 | 61 | 8 | 69 | 5 |
| *Salmonella* | | | | | | | | | |
| 10 | 8 | 1 | 6 | 2 | 5 | 30 | 6 | 159 | 7 |
| 1 | 33 | 11 | 26 | 7 | 0.5 | 93 | 25 | 153 | 70 |
| 0.1 | 37 | 2 | 38 | 5 | 0.05 | 76 | 10 | 86 | 16 |
| 0.01 | 59 | 12 | 75 | 8 | 0.005 | 108 | 7 | 110 | 7 |

Comp A: MOS composition according to example 1
Comp B: MOS composition according to example 2
CELMANAX ™ and SafMannan ®: commercially available yeast derived MOS

TABLE 6

Influence of MOS on relative adhesion of *Salmonella* to ex-vivo broiler or layer chicken ceca tissue

| Animal | Treatment | Adhesion | % Reduction |
|---|---|---|---|
| Broiler | No Treatment | 1.00 | 0 |
| Layer | No Treatment | 0.998 | 0 |
| Broiler | Celmanax | 0.58 | −42 |
| Layer | Celmanax | 0.77 | −23 |
| Broiler | Composition A | 0.37 | −63 |
| Layer | Composition A | 0.72 | −28 |
| Broiler | Composition B | 0.43 | −57 |
| Layer | Composition B | 0.83 | −17 |

Composition A: MOS composition according to example 1
Composition B: MOS composition according to example 2
CELMANAX ™: commercially available yeast derived MOS

TABLE 7

Confirmation of the influence the MOS compositions from this invention have on relative adhesion of *Salmonella* to ceca ex-vivo broiler or laying chicken tissue

| Animal | Treatment | Adhesion | % Reduction |
|---|---|---|---|
| Broiler | No Treatment | 1.00 | 0 |
| | Composition A | 0.60 | −40 |
| | Composition B | 0.59 | −41 |
| Layer | No Treatment | 1.00 | 0 |
| | Composition A | 0.83 | −17 |
| | Composition B | 0.74 | −26 |

Composition A: MOS composition according to example 1
Composition B: MOS composition according to example 2

TABLE 8

Effect of dose of MOS compositions from this invention on relative adhesion of *Salmonella* to ex-vivo ceca chicken tissue

| MOS | Concentration (%) | Adhesion | Reduction (%) |
|---|---|---|---|
| Composition A | 0.002 | 1.26 | +26 |
| | 0.02 | 0.62 | −38 |
| | 0.2 | 0.54 | −36 |
| | 2 | 0.43 | −57 |
| Composition B | 0.002 | 1.27 | +27 |
| | 0.02 | 0.50 | −50 |
| | 0.2 | 0.37 | −63 |
| | 2 | 0.51 | −49 |

Composition A: MOS composition according to example 1
Composition B: MOS composition according to example 2

Results presented in Table 5 show that all MOS containing materials are able to reduce adhesion of *Salmonella* to intestinal epithelial surface. Some MOS sources were more efficient than others. The capacity of MOS to reduce pathogen adhesion to intestinal epithelial cells was confirmed in both young (broiler) and adult (layer) chickens, although the effect was more evident in young broiler chickens (Table 6). These results were further confirmed for the MOS compositions proposed by this current invention on a following test (Table 7). This reduction of adhesion effect is dose-dependent as demonstrated on Table 8. Based on that, a minimal dose of 0.02% was recommended for in vivo trials.

Example 5: In Vivo Trials Immune Modulation

An in vitro assay is performed using macrophages culture in vitro. The macrophages are exposed to the two MOS compositions according to the present invention (Composition A and B). Cells are incubated with prototypes for 1 hour prior to addition of 1 ug/ml LPS (or media sham control), cytokines are measured after 18 hours incubation using ELISA test kit. ELISA is repeated twice. The results of the experiments before and after LSP addition are presented in Tables 9 and 10, respectively.

TABLE 9

In vitro immune response of macrophages exposed to different MOS
NO LPS Challenge

| | TNF-α | | IL-6 | | IL-8 | | IL-10 | |
|---|---|---|---|---|---|---|---|---|
| | pg/ml | % | pg/ml | % | pg/ml | % | pg/ml | % |
| Media | 29.5 | 100 | 4.5 | 100 | 11.2 | 100 | 5.6 | 100 |
| MOS Composition A | 36.5 | 124 | 1.9 | 41 | 15.3 | 136 | 7.9 | 141 |
| MOS Composition B | 33.3 | 113 | 2.0 | 44 | 17.6 | 157 | 8.2 | 146 |

Composition A: MOS composition according to example 1
Composition B: MOS composition according to example 2

TABLE 10

In vitro immune response of LPS challenged macrophages exposed to different MOS
With LPS Challenge

| | TNF-α | | IL6 | | IL-8 | | IL-10 | |
|---|---|---|---|---|---|---|---|---|
| | pg/ml | % | pg/ml | % | pg/ml | % | pg/ml | % |
| rsLPS | 5021 | — | 116 | — | — | — | 27 | — |
| Media + LPS | 9476 | 100 | 4112 | 100 | 766 | 100 | 115 | 100 |
| | (189) | | (3543) | | | | (421) | |
| MOS Composition A | 12997 | 137 | 5692 | 138 | 877 | 115 | 121 | 105 |
| MOS Composition B | 11849 | 125 | 6276 | 153 | 929 | 121 | 124 | 108 |

Composition A: MOS composition according to example 1
Composition B: MOS composition according to example 2

Macrophage cytokine TNF-α, IL-8 and IL-10 increased when exposed to MOS composition A or B, while IL-6 production was decreased by both these MOS compositions compared to control media (Table 9). When macrophages are challenged by LPS, all cytokines are increased by MOS presence (Table 10). These results indicate that the MOS compositions according to the present invention do have a direct effect on the immune system in vitro.

In a follow up test, piglets are fed MOS composition B, at increasing doses (0 to 0.4%) in the diet. Heparinized blood is collected from 8 pigs per treatment for a total of 80 pigs on day 22 post-weaning. Peripheral blood mononuclear cells are isolated using a Ficoll gradient. Cells are plated and stimulated with LPS and the immune response is measured by ELISA for TNFα (pg/ml). These results are presented in Table 11.

TABLE 11

Effect of increasing doses of MOS composition B on ex-vivo
pig macrophage TNFα (pg/ml) response with and without LPS stimulus.

| Condition | Dose of MOS Composition B | | | | | SEM | Model P-value | Linear | Quadratic |
|---|---|---|---|---|---|---|---|---|---|
| | 0.00% | 0.10% | 0.20% | 0.30% | 0.40% | | | | |
| Without LPS | 69.6 | 70.3 | 80.5 | 75.0 | 76.0 | 14.5 | 0.96 | 0.63 | 0.73 |
| With LPS | 852.8 | 1624.0 | 2011.8 | 1646.2 | 2367.2 | 514.3 | 0.22 | 0.04 | 0.63 |

(n = 8),
Composition B: MOS composition according to example 2

The impact of feeding MOS composition B on piglet microphage response was small without LPS challenge but shows a linear increase under LPS challenge. This means that MOS composition B enhances immune response of piglets under disease challenge by modulating TNF-α response.

Example 6: Improvement of GI Health In Vivo

The direct impact of MOS compositions according to the present invention (Composition A and B) on intestinal mucosa cells was investigated using an in vitro C2Be1 cell line culture model that mimics luminal intestinal enterocyte surface. The cells grown on a plate were allowed to form a mucosa-like surface and then incubated with compounds dissolved in media at a 0.2% concentration. Cells were treated with products under serum-limited conditions for 4-5 days.

BrdU ELISA is used to measure the amount of proliferation, where it measures the amount of BrdU incorporated into proliferating cells (the more proliferation, the more BrdU that will be detected in the DNA of the cells). Levels of proliferation are expressed as a ratio calculated by dividing the BrdU incorporation of test wells by that of the controls that has medium only. Value equal to 1 would be equal to average of medium only, meaning no response. The assay is repeated in triplicate on two separate occasions. A compound known to affect cell proliferation called epithelial growth factor (EGF) is used at two different concentrations (10 and 100) positive control. Results can be seen Table 12.

TABLE 12

Effect of MOS A and B and epithelial growth factor (EGF)
at two concentrations on intestinal cells proliferation in vitro.

| | Proliferation Ratio (relative to control = 1) | | % compared to media only (control) | |
|---|---|---|---|---|
| | Mean | SEM | Mean | SEM |
| Composition A | 1.06 | 0.035 | 105.9 | 3.53 |
| Composition B | 1.11 | 0.026 | 110.7 | 2.57 |
| EGF 100 | 1.20 | 0.029 | 119.6 | 2.94 |
| EGF 10 | 1.13 | 0.002 | 113.5 | 0.20 |

(n = 12)
Composition A: MOS composition according to example 1
Composition B: MOS composition according to example 2

Gut health is assessed by comparing the effect of yeast-derived MOS with the MOS compositions A and B on intestinal microbial profile. Samples from ceca of 17 days of age broiler chickens fed MOS from day one were analysed using a custom microarray printed with 16S DNA probes for 100 selected intestinal microbes. Two commercially available yeast-derived MOS products are fed at 0.2% of the diet (BioMos® and CELMANAX™) and one MOS according to the present invention made according to example 1 (35% DP2 and 40% DP3+ on db) is fed at 0.02% of the diet (concentration based results in Table 8). The average relative amount of bacteria DNA that was significantly different between these 3 MOS sources and a negative control diet without MOS was analysed by ANOVA and clustered using JMP Genomics software. The results of the hierarchical clustering analysis are presented on FIG. 2.

Figure 2:
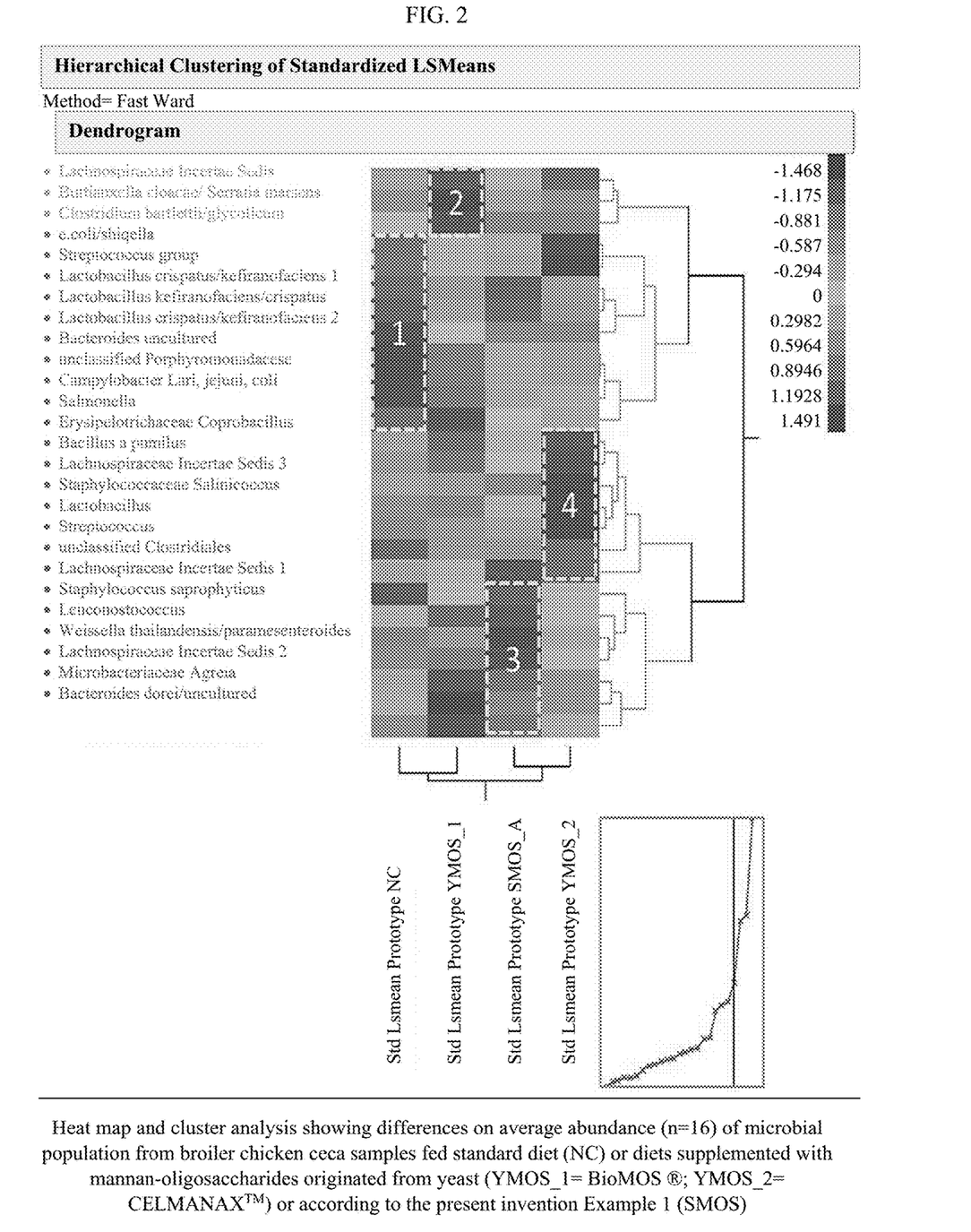
FIG. 2 shows a hierarchical clustering of standardized LSMeans as outlined in Example 6.

Based on the results in FIG. 2 we can see that all MOS products result in a desired reduction of bacteria in cluster 1, which contain pathogen bacteria such as *E. coli*, *Campylobacter* and *Salmonella*. Although, each MOS product achieve this reduction by a simultaneous increase on bacteria from a different cluster (cluster 2 for BioMOS®, cluster 4 for CELMANAX™ and cluster 3 for the MOS composition Example 1 of this current invention).

Example 7: Increase of Growth Performance In Vivo

Chickens

A first study (Trial 1) was designed to compare MOS composition according to Example 1 and Example 2 of the present invention with commercially available yeast-derived MOS. Polydextrose produced by a similar process as the process described in Example 1 (wherein dextrose and sorbitol are used as reactants) was also added to show the importance of these composition being polymannose. MOS composition of Example 1 and 2 were added in two extreme doses (0.02 and 2%) in the diet of broiler chickens challenged with *Salmonella enteritidis*, while the yeast-derived MOS (CELMANAX™ and BioMOS®) were added at the recommended dose of 0.2% in the diets. Performance parameters and *Salmonella* level in the ceca were measured at 28 days of age. Results can be seen in Table 13.

TABLE 13

Effect of different MOS compositions added to diets of Salmonella enteritidis challenged broiler chicken diets on mortality. European Broiler Index (EPI), body weight (BW), average daily body weight gain (ADG), average daily feed intake (ADFI), feed to gain (F:G) and gain to feed (G:F) ratio, and Salmonella enteritidis counts in the ceca at 20 days of age.

| | Product | | | | | |
|---|---|---|---|---|---|---|
| | Control | Antibiotic | Composition A | Composition A | Composition B | Composition B |
| | | | | Dose (%) | | |
| | — | | 0.02 | 2.00 | 0.02 | 2.00 |
| | | | | $n^1$ | | |
| | 9 | 9 | 9 | 9 | 9 | 9 |
| | | | Performance | | | |
| Mortality, % | 0.05 | 1.90 | 3.80 | 1.90 | 3.70 | 0.05 |
| EPI | $364^{abc}$ | $384^a$ | $375^{ab}$ | $326^e$ | $355^{bcd}$ | $329^{de}$ |
| EPI excluding mortality | $364^{bc}$ | $392^a$ | $391^a$ | $332^d$ | $368^b$ | $329^d$ |
| BW 0d, g | 45.8 | 44.9 | 46.3 | 45.6 | 45.5 | 45.1 |
| BW 20d, g | $927^{bcd}$ | $973^{ab}$ | $997^a$ | $863^{ef}$ | $939^{bcd}$ | $851^f$ |
| ADG 0-20d, g | $44.1^{bcd}$ | $46.4^{ab}$ | $47.5^a$ | $40.9^e$ | $44.7^{bcd}$ | $40.3^e$ |
| ADFI 0-20d, g | $56.1^{bcd}$ | $57.6^{ab}$ | $60.6^a$ | $53.1^{cde}$ | $56.9^b$ | $52.1^e$ |
| F:G 0-20d | $1.273^{ef}$ | $1.241^g$ | $1.275^{def}$ | $1.300^a$ | $1.273^{def}$ | $1.294^{abc}$ |
| G:F 0-20d | $0.786^{bc}$ | $0.806^a$ | $0.785^{bc}$ | $0.769^e$ | $0.785^{bc}$ | $0.773^{de}$ |
| | | | Salmonella | | | |
| cfu/g ceca content | $4.23E+05^{bc}$ | $0.00E+00^d$ | $4.67E+05^{bc}$ | $9.71E+05^b$ | $2.75E+05^{bc}$ | $1.08E+06^b$ |
| Relative Presence (% of Control) | 100 | 0 | 110 | 230 | 65 | 254 |

| | Product | | | | | |
|---|---|---|---|---|---|---|
| | Polydextrose | Polydextrose | BioMOS | Celmanax | | |
| | | Dose (%) | | | | |
| | 0.02 | 2.00 | 0.20 | 0.20 | Pooled | |
| | | $n^1$ | | | SEM | P-value |
| | 9 | 9 | 9 | 9 | — | — |
| | | | Performance | | | |
| Mortality, % | 3.80 | 0.05 | 3.80 | 1.90 | — | 0.998 |
| EPI | $355^{abcd}$ | $350^{bcde}$ | $356^{abcd}$ | $365^{abc}$ | 10.1 | <.0001 |
| EPI excluding mortality | $371^{ab}$ | $350^{bcd}$ | $371^{ab}$ | $372^{ab}$ | 7.99 | <.0001 |
| BW 0d, g | 46.6 | 45.7 | 46.1 | 45.9 | 0.47 | 0.532 |
| BW 20d, g | $938^{bcd}$ | $897^{cdef}$ | $918^{bcde}$ | $950^{abc}$ | 20.3 | <.0001 |
| ADG 0-20d, g | $44.6^{bcd}$ | $42.6^{cde}$ | $44.7^{abcd}$ | $45.2^{abc}$ | 0.97 | <.0001 |
| ADFI 0-20d, g | $56.3^{bcd}$ | $54.6^{bcde}$ | $56.7^{bc}$ | $57.7^{ab}$ | 1.25 | <.0001 |
| F:G 0-20d | $1.265^f$ | $1.282^{abcdef}$ | $1.268^f$ | $1.277^{cdef}$ | 0.007 | <.0001 |
| G:F 0-20d | $0.791^b$ | $0.780^{bcde}$ | $0.789^b$ | $0.783^{bcd}$ | 0.004 | <.0001 |
| | | | Salmonella | | | |
| cfu/g ceca content | $6.24E+05^{bc}$ | $1.04E+06^b$ | $3.54E+06^a$ | $1.79E+05^c$ | — | <.0001 |
| Relative Presence (% of Control) | 148 | 246 | 839 | 42 | — | — |

$n^1$: replicates per treatment.
Composition A: MOS composition according to example 1
Composition B: MOS composition according to example 2
CELMANAX ™ and BioMOS: commercially available yeast derived MOS
Mortality: percentage of total mortality and culling relative of the number of birds at day 0;
EPI: European poultry index ((final body weight (g) × (l00% − mortality %)/(10 × period in days) × overall F:G));
EPI excluding mortality: ((final body weight (g) × 100%))/((10 × period in days) × overall F:G));
BW: body weight (g):
ADG = average daily gain (g):
ADFI: average daily feed intake (g);
F:G : feed to gain ratio (g feed intake:g body weight gain);
G:F : gain to feed ratio (g body weight gain:g feed intake).
$^{a,b,c,d,e,f,g}$means within a row without common subscript differ significantly (p < 0).

The best broiler performance at 20 days of age were obtained with Composition A at 0.02%, which resulted in better EPI (excluded mortality), body weight, weight gain and feed intake compared to control. In comparison to other treatments, Composition A was numerically superior to all and statistically superior to birds fed Composition A 2.00%, Composition B (any dose), polydextrose (any dose, except EPI excluding mortality). When compared to yeast-derived MOS, only CELMANAX™ had similar body weight, weight gain or feed intake as Composition A. As differences in feed utilization were correlated to differences in feed intake, we can conclude that these differences in performance were actually driven by feed intake. MOS Compositions A and B, as well as CELMANAX™, do not affect *Salmonella* counts in the ceca when compared to control birds, while yeast-derived BioMOS® increases the presence of *Salmonella* (Table 13). These results are aligned with in vitro observations that MOS products are not bactericidal, but some yeast-derived MOS can stimulate pathogenic bacteria growth (Table 2).

Based on results of Trial 1, a dose-response study (Trial 2) is designed to identify the best dose of MOS Composition A to be added into broiler chicken diets. The doses tested ranged from 0.01 to 1.00%. Results presented on Table 14 show that the effects of MOS Composition A are quadratic in nature for body weight, daily gain, feed intake and feed to gain ratio, with the best dose at 0.02%. These results confirm the importance of dose when feeding a more pure MOS source and the identified dose was also aligned with in vitro results (Table 8) and with results of Trial 1 (Table 13).

TABLE 14

Effect of increasing doses of mannan-oligosaccharide (MOS) Composition A in the diet on performance of broiler chickens up to 20 days of age.

| MOS | Composition A | | | | | | Pooled | | Contrasts | |
|---|---|---|---|---|---|---|---|---|---|---|
| Level (%) | 0.00 | 0.01 | 0.02 | 0.20 | 0.60 | 1.00 | SEM | P-value | Linear | Quadratic |
| EPI | 282 | 292 | 302 | 287 | 291 | 284 | 6.56 | 0.537 | ns | ns |
| BW 0d, g | 39.3 | 39.8 | 40.1 | 40.1 | 39.7 | 39.4 | 0.75 | 0.839 | ns | ns |
| BW 28d, g | 1726 | 1729 | 1765 | 1706 | 1685 | 1692 | 21.2 | 0.129 | ns | ** |
| ADG 0-28d, g | 60.2 | 60.3 | 61.6 | 59.5 | 58.8 | 59.0 | 0.75 | 0.124 | ns | ** |
| ADFI 0-28d, g | 84.1 | 83.6 | 85.9 | 82.3 | 81.0 | 81.7 | 1.14 | 0.021 | ns | *** |
| F:G 0-28d | 1.397 | 1.386 | 1.394 | 1.382 | 1.379 | 1.385 | 0.007 | 0.479 | ns | |

Composition A: MOS composition according to example 1
EPI = European poultry index ((final body weight (g) × (100% − mortality %)/((10 × period in days) × overall F:G));
BW = body weight (g);
ADG = average daily gain (g);
ADFI = average daily feed intake (g);
F:G = feed to gain ratio (g feed intake:g body weight gain).
(*, , *) contrast significant at $p < 0.05$, 0.01 or 0.001, respectively.

Two additional animal feeding tests are used to confirm the recommended dose of 0.02% Composition A in poultry diets. The third study (Trial 3) tests feeding Composition A in diets with or without antibiotic growth promoter chlortetracycline (CTC). The forth study (Trial 4) tests feeding the same product and dose to laying hens during the laying period from 18 to 30 weeks of age. The results of these studies can be seed in Tables 15 and 16, respectively.

TABLE 15

Performance of broiler chickens fed diets with antibiotic growth promoter chlortetracycline (CTC), MOS composition A or their combination up to 35 days of age.

| | Control | CTC | Composition A | Composition A + CTC | p-value | STD error |
|---|---|---|---|---|---|---|
| BW0 | $40.0^{ns}$ | $40.2^{ns}$ | $40.0^{ns}$ | $40.2^{ns}$ | 0.301 | 0.10 |
| BW35 | $1854.7_c$ | $1978.6^b$ | $1956.6^b$ | $2047.0^a$ | <.0001 | 14.91 |
| ADG 0-35 | $51.8_c$ | $55.4^b$ | $54.8^b$ | $57.3^a$ | <.0001 | 0.43 |
| ADFI 0-35 | $92.0^a$ | $90.8_c$ | $90.7_c$ | $91.1^b$ | <.0001 | 0.05 |
| F:G 0-35 | $1.77^a$ | $1.64^b$ | $1.66^b$ | $1.59_c$ | <.0001 | 0.01 |

Composition A: MOS composition according to example 1
CTC = chlortetracycline;
BW = body weight (g);
ADG = average daily gain (g);
ADFI = average daily feed intake (g);
F:G = feed to gain ratio (g feed intake:g body weight gain).
$^{a,b,c}$means within a row without common subscript differ significantly ($p < 0.05$)
(n = 9 replicates per treatment, 50 birds per replicate)

TABLE 16

Performance of laying hen chickens fed MOS Composition A or B.

|  | Control | Composition A | Composition B | P-value |
|---|---|---|---|---|
| ADFI, g/hen/day | 98.73 ± 0.04 | 98.53 ± 0.21 | 98.57 ± 0.11 | 0.776 |
| Egg wt, g | 47.80 ± 0.99 | 48.02 ± 0.93 | 47.10 ± 0.98 | 0.966 |
| Albumen wt., g | 29.82 ± 0.41 | 30.42 ± 0.66 | 29.19 ± 0.53 | 0.527 |
| Yolk wt. | 11.35 ± 0.41 | 11.55 ± 0.36 | 11.29 ± 0.34 | 0.978 |
| Shell wt, g | 6.88 ± 0.14$^a$ | 5.64 ± 0.38$^b$ | 6.79 ± 0.12$^a$ | 0.0002 |
| Shell thickness, mm | 0.43 ± 0.008 | 0.44 ± 0.006 | 0.44 ± 0.004 | 0.472 |
| Mortality (no.) | 0 | 0 | 0 | — |
| Laying percentage (hen egg Production %) | 65.14 | 68.47 | 66.41 | 0.1468 |
| Hen house egg Production % | 59.27$^b$ | 62.30$^a$ | 60.43$^{ab}$ | 0.1468 |
| Number of eggs produced | 644$^b$ | 675$^a$ | 652$^{ab}$ | 0.0922 |
| Feed Conversion (g feed/dosen eggs) | 1.817$^a$ | 1.726$^b$ | 1.784$^{ab}$ | 0.0687 |

Composition A: MOS composition according to example 1
Composition B: MOS composition according to example 2
ADFI = average daily feed intake (g);
wt = weight (g).
$^{(a, b)}$ means within a row without common subscript differ significantly according to p-value specified.
(n = 7 replicates per treatment, 10 birds per replicate)

Results of Trial 3 (Table 15) show that both antibiotic growth promoter CTC and MOS Composition A presented in this current invention (dose 0.02%) resulted in overall better performance of broiler chickens compared to control treatment with no additive. Even more, the combination of antibiotic growth promoter CTC and MOS Composition A resulted in a symbiotic further improvement in performance compared to their individual effects (Table 15). Based on these results we can conclude that MOS Composition A presented in this current invention brings beneficial effects on broiler chicken performance in diets with or without antibiotic growth promoters.

Results of Trial 4 (Table 16) show no effect of MOS Compositions A or B fed in laying hen diets on average daily feed intake or most egg characteristics (egg weight, albumen weight, yolk weight, eggshell thickness or mortality). Eggshell thickness was significantly reduced by MOS Composition A, although shell thickness is not a risk to egg quality for laying hens in this studied period (18-10 weeks of age). The main effect observed when feeding MOS described in this current invention to laying hens was an increase in the number of eggs laid and improvement in the conversion of feed into eggs (Table 16). This effect was more evident for MOS Composition A than for Composition B.

Pig

A piglet study (Trial 5) was carried out to compare the effects of feeding mannan-oligosaccharides from this current invention (Composition A and B) with commercially available yeast-derived product BioMOS®. This same trial was used to determine the best dose of MOS composition A or B to be added to piglet diets. Results of Trial 5 are presented in Table 17.

TABLE 17

Effect of feeding yeast-derived mannan-oligosaccharide (MOS) or MOS Composition A and B at different doses on performance of piglets up to 42 days post-weaning.

| | A | B | C | D | E | F | G | H | |
| --- | --- | --- | --- | --- | --- | --- | --- | --- | --- |
| | | | Product | | | | | | |
| | Control | BioMos | Composition A | | | Composition B | | | |
| | | | Dose (%) | | | | | | |
| | | 0.20% | 0.02% | 0.20% | 0.50% | 0.02% | 0.20% | 0.50% | SEM |
| BW0 (kg) | 6.46 | 6.56 | 6.39 | 6.49 | 6.42 | 6.50 | 6.27 | 6.47 | 0.421 |
| BW42 (kg) | 25.79 | 24.72 | 25.62 | 27.22 | 25.58 | 24.60 | 27.61 | 24.95 | 0.844 |
| ADG (kg) | 0.45 | 0.42 | 0.45 | 0.48 | 0.44 | 0.44 | 0.49 | 0.45 | 0.019 |
| ADFI (kg) | 0.63 | 0.59 | 0.61 | 0.67 | 0.62 | 0.58 | 0.69 | 0.60 | 0.028 |
| F:G | 1.43 | 1.43 | 1.40 | 1.41 | 1.45 | 1.41 | 1.43 | 1.43 | 0.045 |

| | Contrasts | | | Composition A | | Composition B | |
| --- | --- | --- | --- | --- | --- | --- | --- |
| | A vs B | A vs D | A vs G | Linear | Quadratic | Linear | Quadratic |
| BW0 (kg) | 0.546 | 0.854 | 0.269 | 0.965 | 0.651 | 0.885 | 0.154 |
| BW42 (kg) | 0.356 | 0.217 | 0.118 | 0.971 | 0.109 | 0.899 | 0.0139* |
| ADG (kg) | 0.333 | 0.198 | 0.101 | 0.966 | 0.094 | 0.814 | 0.0292* |
| ADFI (kg) | 0.360 | 0.235 | 0.106 | 0.968 | 0.097 | 0.961 | 0.0091* |
| F:G | 0.940 | 0.324 | 0.969 | 0.162 | 0.199 | 0.700 | 0.871 |

Composition A: MOS composition according to example 1
Composition B: MOS composition according to example 2
BioMOS: commercially available yeast derived MOS Results of Trial 5 showed that yeast-derived MOS (Bio-MOS®) or MOS Composition A had no effect on piglet performance while MOS Composition B of this current invention had a quadratic effect on body weight, average daily gain and average feed intake (Table 17). The best dose of MOS Composition B to be included in piglet diets is 0.2%.

The invention claimed is:

1. A mannose oligosaccharide composition comprising:
a mannose oligosaccharide content of mannose oligosaccharide having a degree of polymerization (DP) of 3 or more that is 30 wt % db or higher; and
a dimannose content of from 10 to 35 wt % db;
wherein the composition has a water solubility of from 20 to 90% measured as a 10 wt % aqueous solution of the composition at 40° C.

2. The composition of claim 1 characterized in that it comprises less than 0.1 wt % db of beta-glucan.

3. The composition of claim 1 characterized in that it has a mannose oligosaccharide content of mannose oligosaccharide having a degree of polymerization (DP) of 3 or more that is 60 wt % db or higher.

4. The composition of claim 1 characterized in that it has a dimannose content of from 10 to 25 wt % db.

5. The composition of claim 1 characterized in that it has a fructose content of 0.5 to 10 wt % db.

6. A food, animal feed or pet food product comprising the composition of claim 1 and further food, animal feed or pet food ingredients.

7. The food, animal feed or pet food product of claim 6 wherein the composition of claim 1 is present in an amount of from 0.1 to 0.5 wt % based on the weight of the food, animal feed or pet food product.

8. The food, animal feed or pet food product of claim 6 wherein the composition of claim 1 is present in an amount of from 0.01 to 0.05 wt % based on the weight of the food, animal feed or pet food product.

9. The composition of claim 1 for treating human or animal.

10. The composition of claim 1 for reducing or preventing bacterial attachment to the intestinal mucosa and/or for improving weight gain and/or improving feed intake and/or improving body weight gain and/or improving stool quality in human or animal.

11. The composition of claim 1 characterized in that it has a mannose content of 5 to 25 wt % db.

12. The composition of claim 1 characterized in that it has a glucose content of 1 to 15 wt % db.

13. A cosmetic, personal care or pharmaceutical product comprising the mannose oligosaccharide composition according to claim 1, wherein the cosmetic product is a makeup cream, makeup lotion or lipstick; the personal care product is an oral care product, hair care product, skin care product or hygiene product; or the pharmaceutical product is a disinfectant or an antiseptic balm.

14. A mannose oligosaccharide composition that has a water solubility of from 20 to 90% measured as a 10 wt % aqueous solution of the composition at 40° C. and that comprises less than 0.1 wt % db of beta-glucan, has a mannose oligosaccharide content of mannose oligosaccharide having a degree of polymerization (DP) of 3 or more that is 30 wt % db or higher, and has a dimannose content of from 10 to 35 wt % db.

15. The composition of claim 14 characterized in that it has having a fructose content of 0.5 to 10 wt % db, a mannose content of 5 to 25 wt % db, and/or a glucose content of 1 to 15 wt % db.

16. A process for making the mannose oligosaccharide composition of claim 1, comprising:
a) polycondensing mannose by passing the mannose through a microreactor at a temperature of from 180° C. to 240° C. in the presence of an acidifying catalyst to produce manno-oligosaccharide composition, b) optionally neutralising and/or decolorizing the manno-oligosaccharide composition, and c) collecting the manno-oligosaccharide composition.

17. The process according to claim 16 wherein the residence time of mannose in the microreactor during step a) is from 5 to 20 seconds.

* * * * *

UNITED STATES PATENT AND TRADEMARK OFFICE
CERTIFICATE OF CORRECTION

| | | |
|---|---|---|
| PATENT NO. | : 11,771,124 B2 | Page 1 of 1 |
| APPLICATION NO. | : 16/622641 | |
| DATED | : October 3, 2023 | |
| INVENTOR(S) | : Bruno Frédéric Stengel et al. | |

It is certified that error appears in the above-identified patent and that said Letters Patent is hereby corrected as shown below:

On the Title Page

Under "OTHER PUBLICATIONS", insert -- "Research and application of mannan-oligosaccharides", Kou Qing et al., Cereal & Feed Industry, no. 5 of 2012, pages 57-59 --.

Under "OTHER PUBLICATIONS", insert -- A.A. Kubasov "Chemical kinetics and catalysis. Part 1", Moscow: Editorial House of Moscow University, 2004, pages 2 to 3 --.

Under "OTHER PUBLICATIONS", insert -- Chemical Encyclopedia, editor Knunyants, I.L., Scientific Editorial House "The Great Russian Encyclopedia", 1992, volume 3, page 375 --.

In the Specification

In Column 2, Line 52, delete "generally" and insert -- generally, --, therefor.

In Column 2, Line 52, delete "example" and insert -- example, --, therefor.

In Column 2, Line 53, delete "limitation" and insert -- limitation, --, therefor.

In Column 4, Line 24, delete "3 1wt % db." and insert -- 31 wt % db. --, therefor.

In Column 4, Line 56, delete "Detection".

In the Claims

In Column 26, Lines 24-25, in Claim 15, delete "characterized in that it has".

Signed and Sealed this
Fifth Day of December, 2023

Katherine Kelly Vidal
*Director of the United States Patent and Trademark Office*